United States Patent [19]

Rogers

[11] 4,015,608

[45] Apr. 5, 1977

[54] LARYNGECTOMY LUNG PROTECTOR

[75] Inventor: William F. Rogers, Maggie, N.C.

[73] Assignee: Lawrence Peska Associates, Inc., New York, N.Y. ; a part interest

[22] Filed: Oct. 8, 1975

[21] Appl. No.: 620,576

[52] U.S. Cl. .............................. 128/351; 128/203; 128/142.2

[51] Int. Cl.$^2$ ........................................ A61M 16/00

[58] Field of Search ............ 128/351, 145.5, 145.7, 128/145.8, 147, 142.2, 188

[56] References Cited

UNITED STATES PATENTS

| | | | |
|---|---|---|---|
| 1,266,624 | 5/1918 | Ramsay | 128/145.7 |
| 3,185,147 | 5/1965 | Champagne | 128/147 |

*Primary Examiner*—Robert W. Michell
*Assistant Examiner*—Henry J. Recla

[57] ABSTRACT

A laryngectomy lung protector is disclosed comprising breathing apparatus which is insertable in the throat in the region of the larynx and is sealed to the throat by means of an adjustable seal encircling and slidably placed on the apparatus which can be moved toward or away from the throat. The apparatus is a hollow frustocone, the base of which is sealed and the frustum end of which is inserted in the throat. By moving the cone inwardly or outwardly the diameter inserted in an opening in the throat can be adjusted. Valved air inlet and outlet passages in the cone allow passage of air into and out of an opening in the throat through the frustum end. The inlet valve is connected to a tank containing compressed air or oxygen. A breathing regulator valve may also be used in combination with the tank.

3 Claims, 2 Drawing Figures

LARYNGECTOMY LUNG PROTECTOR

SUMMARY OF THE INVENTION

The present invention relates to breathing apparatus comprising a hollow frusto-cone the frustum end of the cone being insertable in an opening in the throat in the region of the larynx, the base of the cone being sealed by a plate member. An air inlet passage for directing air toward and out of the frustum end of the cone and an air outlet passage for leading air away from the frustum end of the cone are also provided in the cone. A first valve member comprising in combination a first by-pass valve and a first check valve are operatively connected to the air inlet passage, and a second valve member comprising in combination a second by-pass valve and a second check valve are operatively connected to the outlet passage, both the first valve and the second valve and the second valve members respectively controlling the flow of air into and out of the air inlet and air outlet passage in the cone. An adjustable seal member is mounted on and encircles the cone toward the frustum end for forming an adjustable seal between the outer wall of the cone and a throat opening. The air inlet and the first valve member are operatively connected to a breathing regulator valve and an air tank through the first check valve. A belt secured to the cone for holding the cone in place on the neck of a wearer is also provided, the belt being mounted on the cone between the adjustable seal and the base of the cone. The edges of the belt extend beyond the seal for a distance sufficient for the edges to seal the belt to the neck of a wearer in the area where the cone is held in place.

DETAILED DESCRIPTION

Figures 1, 2:
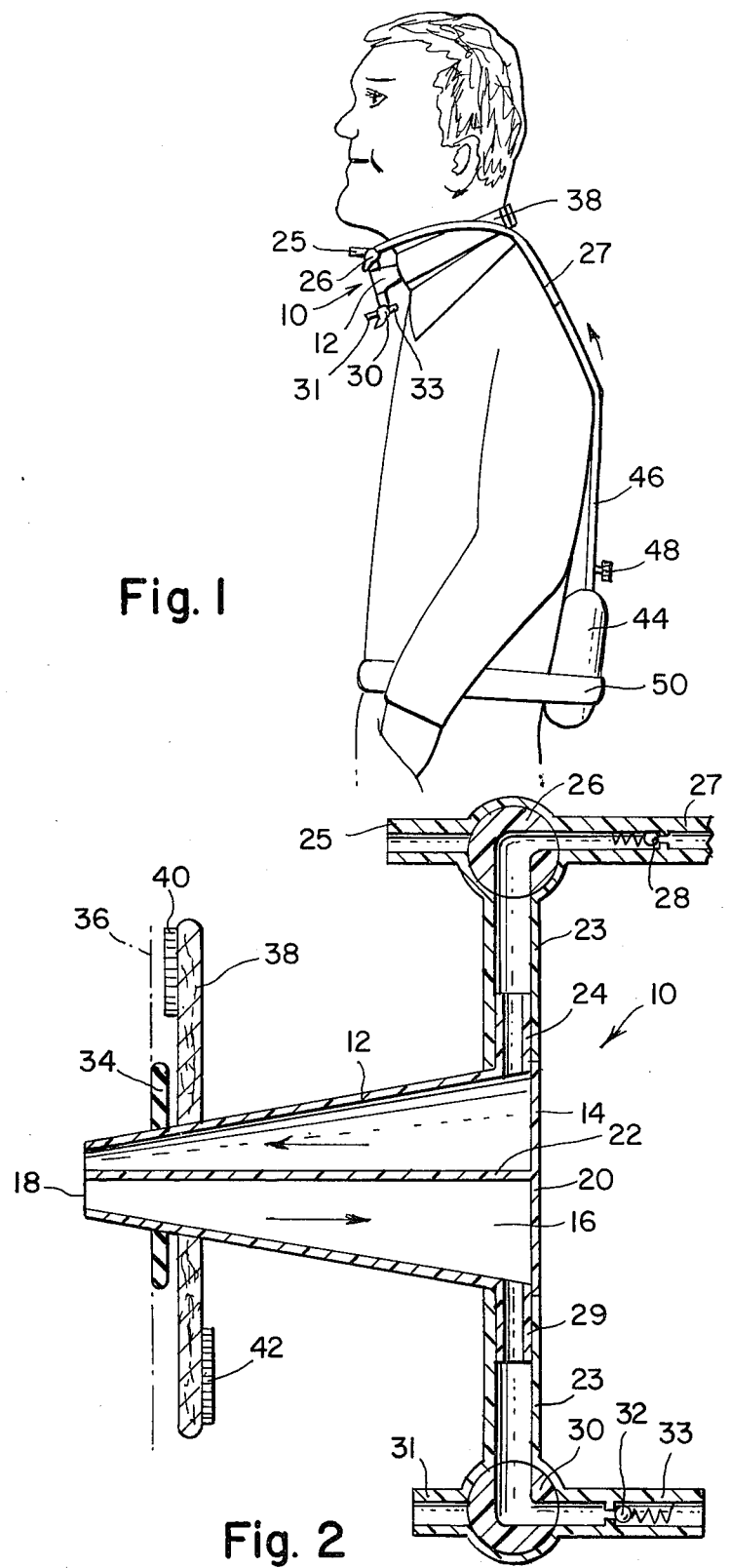
FIG. 1 illustrates a perspective view of a person wearing breathing apparatus in which the apparatus is inserted in an opening in the throat of a wearer in the region of the larynx according to one embodiment of the present invention.
FIG. 2 illustrates a side elevation in section of breathing apparatus comprising a hollow frusto-cone, the frustum end of which is insertable in an opening in the throat of a wearer, valve members also being provided to control the flow of air into and out of the cone according to an embodiment of the present invention.

Surgical procedure for the removal of the larynx or a laryngectomy involves the diversion of the trachea to a permanent surgically provided opening in the throat. Breathing through this opening supplants normal breathing through the nose or mouth. Although devices are available such as electronic larynxes to enable laryngectomy patients to speak, other activities of persons having had this procedure performed on them are greatly curtailed if not prohibited. Generally, any activity involving water sports such as swimming, fishing from a boat, water skiing and the like are restricted as well as other activities where air-borne contaminants are a hazzard such as painting where fumes are heavy and wood working where a great deal of dust is generated. Most of the devices of the prior art which are insertable in the trachea through an opening in the throat in the region of the larynx are artificial voice boxes or larynxes. Devices of this type are illustrated by U.S. Pat. Nos.: 3,066,674, Capra; 2,405,851, Roberts; 2,058,212, Burchett; 2,024,601, Riesz; 1,993,076, Sheard et al; 1,867,350, Burchett; 1,840,112, Lane and 1,633,705, McKesson. None of these references describe apparatus which aids the breathing of a laryngectomy patient.

It is therefor an object of the present invention to overcome these and other difficulties encountered in the prior art.

It is a further object of the present invention to provide novel apparatus which aids the breathing of persons who have had a laryngectomy.

It is a further object of the present invention to provide novel breathing apparatus for insertion in an opening in the throat in the region of the larynx and which allows its user to breath in an environment in which there is air contamination or potential contamination.

These an other objects have been achieved according to the present invention and will become apparent from the disclosure and claims that follow as well as the appended drawings.

Referring to the drawing in FIGS. 1 and 2, breathing apparatus 10 is provided for the protection of the lungs of a person who has had a laryngectomy and comprises a hollow frusto-cone 12 having an air inlet passage 14 and fitting 24 at the base of the cone for directing air toward and out of the frustum end 18, the base of the cone 12 being sealed by plate 20. The cone is divided into air inlet passage 14 and air outlet passage 16 by means of plate 22, the air outlet passage directing the flow of air from the frustum end 18 of the cone to the fitting 29. A first valve assembly for controlling the flow of air into the cone 12 is provided comprising first by-pass valve 26 for directing the flow of air from tube 27 to tube 23 or the flow of air from tube 25 to tube 23. Tube 27 has a spring biased ball type check valve 28 mounted therein for directing the flow of air in one direction toward cone 12. A second valve assembly for controlling the flow of air out of cone 12 is provided comprising second by-pass valve 30 for directing the flow of air from tube 23 to tube 33 or the flow of air from tube 23 to tube 31. Tube 33 has a spring biased ball type check valve 32 mounted therein for directing the flow of air in one direction away from cone 12. An adjustable seal member comprising a soft and resillient torroidal seal 34 is mounted toward and encircles the frustum end of cone 12, seal 34 being slideable in a direction from the frustum toward the base of the cone 12. An adjustable belt 38 is secured to the cone 12, the ends of the belt terminating in opposing adjustable fastener members 40 and 42 such as adhesive fasteners, mechanical fasteners such as snaps, hooks and eyes or VELCRO (trademark) fasteners. The belt 38 is preferably made of a soft pliable material and is of a size such that edges of the belt extend transversely beyond the seal 34 for a distance sufficient for these edges to seal the belt to the neck of a wearer in the area where the belt is held in place on the neck. A tube 46 is connected to tube 27, tube 46 leading into regulator valve 48 attached to compressed air or compressed oxygen tank 44 held to the body of a person using the apparatus 10 by means of belt 50. The regulator valve 48 is an art-known valve used in devices such as oxygen masks or self contained under water breathing apparatus which is commonly known as SCUBA apparatus and allows the flow of air or oxygen out of the tank 44 when pressure is drawn on valve 48 by inhalation.

In use the valve 10 is effectively sealed in an opening in the throat by three sealing functions, the first of which comprises the arrangement of the cone 12 whereby the frustum end thereof is inserted in a throat opening and the diameter of the cone is selected at the frustum end that most snugly fits the throat opening. This diameter is determined by a trial and error method by moving the frustum end in and out of the throat opening until the most comfortable and snugest fit are obtained. The frustum end of the cone may then be shortened by trimming in after which the second sealing operation is performed whereby seal 34 is moved toward the frustum end of the cone and into a substantially sealing relation with outer throat wall 36. The third sealing operation is performed by pulling belt 38 snugly around the neck so that the edges thereof transverse to the longitudinal direction of the belt seal themselves snugly to the neck of a person wearing the apparatus 10. Belt 38 also functions to hold seal 38 in place against the neck 36. Valve 26 is adjusted to allow air to flow from tube 27 into tube 23. Valve 30 is also adjusted to allow air to flow from tube 23 into tube 33 after which valve 48 is opened to allow air to flow into the apparatus 10 when it is inhaled on.

Although the invention has been described by reference to some embodiments it is not intended that the novel apparatus be limited thereby but that modifications thereof are intended to be included as falling within the broad scope and spirit of the foregoing disclosure, the following claims and the appended drawing.

What is claimed is:

1. Breathing apparatus comprising hollow frusto-cone means having a base extending toward a tapered end, said tapered end of said cone being insertable in an opening in the throat in the region of the larynx, said base of said cone being sealed by plate means, said cone having air inlet passage means for directing air toward and out of the tapered end of said cone, air outlet passage means for leading air away from the tapered end of said cone, first valve means for controlling the flow of air into said air inlet passage, second valve means for controlling the flow of air out of said air outlet passage, adjustable seal means slidably mounted on and encircling said cone toward the tapered end of said cone for forming an adjustable seal between the outer wall of said cone and a throat opening, said first valve means comprises first check valve means for leading air into said air inlet passage and first by-pass valve means for diverting the flow of air into said air inlet passage from said first check valve or the ambient air surrounding said breathing device, said second valve means comprising second check valve means for leading air out of said air outlet passage and second by-pass valve means for diverting the flow of air from said air outlet passage to said second check valve or the ambient air surrounding said breathing device.

2. The breathing apparatus of claim 1 having belt means secured thereto for holding said apparatus in place on the neck of a wearer.

3. The breathing apparatus of claim 2 where said first check valve is operatively connected to breathing regulator means and tank means for holding a breathable gas under pressure.

* * * * *